United States Patent [19]

Clark et al.

[11] Patent Number: 4,877,729

[45] Date of Patent: Oct. 31, 1989

[54] RECOMBINANT DNA ENCODING NOVEL FAMILY OF PRIMATE HEMATOPOIETIC GROWTH FACTORS

[75] Inventors: Steven C. Clark, Winchester; Agnes B. Ciarletta, Tewksbury; Yu-Chung Yang, Arlington, all of Mass.

[73] Assignee: Genetics Institute, Inc., Cambridge, Mass.

[21] Appl. No.: 916,335

[22] Filed: Oct. 7, 1986

Related U.S. Application Data

[63] Continuation-in-part of Ser. No. 885,060, Jul. 14, 1986, abandoned, and Ser. No. 893,764, Aug. 6, 1986, abandoned.

[51] Int. Cl.[4] .................... C12P 21/02; C12N 15/00; C12N 1/00
[52] U.S. Cl. .................... 435/68; 435/172.3; 435/320; 935/9; 935/10; 935/11; 935/13
[58] Field of Search .................... 435/172.3, 68, 70; 935/9, 10, 11, 13

[56] References Cited

U.S. PATENT DOCUMENTS 4,658,018 3/1984 Urdahl et al.

FOREIGN PATENT DOCUMENTS 60-207594 10/1985 Japan .
60-207595 10/1985 Japan .
WO85/02863 7/1985 PCT Int'l Appl. .

OTHER PUBLICATIONS

Stadler et al, Chemical Abstracts, vol. 106, 16853y (1987).
Suzuki et al, Chemical Abstracts, vol. 105, 224285w (1986).
Stadler et al, Chemical Abstracts, vol. 103, 525575f (1985).
Campbell et al, Eur. J. Biochem., vol. 150, pp. 297–304 (1985).
Palacios, The J. of Immunology, vol. 132, pp. 1833–1836, Apr. 1984.
Ythier et al, PNAS USA, vol. 82, pp. 7020–7024, Oct. 1985.
Conlon et al, The J. of Immunology, vol. 135, pp. 328–332, Jul. 1985.
Ihle et al, The J. of Immunology, vol. 131, pp. 282–287 (1983).
Goossens et al, Methods on Enzymology, vol. 76, pp. 805–817 (1981).
Scott et al, PNAS USA, vol. 78, pp. 4213–4217, Jul. 1981.
Yokota et al, PNAS USA, vol. 81, pp. 1070–1074, Feb. 1984.
Fung et al, Nature, vol. 307, pp. 233–237, Jan. 19, 1984.
Boston Globe, Oct. 7, 1986, "Major Find in Blood Science is Reported" 230(99):1,11.
New York Times, Oct. 7, 1986, "Researchers Find Important Factor In Blood Growth", cxxxvi(46,920):p.C3.
Stadler et al, 1986, "Biological and Biochemical Characteristics of . . . (BaPA) . . . ", Immunbiol., 172-22-5-230.
Suzuki et al, Nov. 1986, "Production of a Cytokine . . . ," J. Exp. Med., 164:1682–1699.
Stadler et al, 1986, "Distinction of the Human Basophil Promoting Activity from Interleukin-3", Int. Archs Allergy Appl, Immunology, 77:151–154.
Stadler & Hirai, 1988, "Human Growth Factors for Metachromatically Staining Cells," Lymphokines, vol. 15, pp. 341–354.
Hirai, de Weck & Stadler, 1988, "Characterization of a Human Basophil-Like Cell Promoting Activity": J. Immunol, 140:221–227.
Godard et al, 1988, "Biochemical Characterization and Purification of Hilda . . . ," Blood, 71(6):1618–1623.
Ihle, 1985, "Immunological Regulation of Hematopoietic Stem Cell Differentiation by Interleukin-3" in the Yeat in Immunology, 1984–85, pp. 107–117.

(List continued on next page.)

Primary Examiner—Alvin E. Tanenholtz
Attorney, Agent, or Firm—David L. Berstein; Bruce M. Eisen; Mary E. Bak

[57] ABSTRACT

A novel family of primate IL-3-like polypeptides is provided via recombinant techniques.

12 Claims, 2 Drawing Sheets

OTHER PUBLICATIONS

Cohen et al, 1986, "Cloning and Expression of the Rat Interleukin-3 Gene", *Nucleic Acids Research*, 14(9):3641-3658.

Kindler et al, 1986, "Stimulation of Hematopoiesis...", *Proc. Natl. Acad. Sci*, USA, 83:1001-1005.

Emerson et al, 1985, "Purification of Fetal Hematopoietic Progenitors...", *J. Clin. Invest.*, 76:1286-1290.

Yang et al, Oct. 10, 1986, "Human IL-3...", *Cell*, 47:3-10.

Griffin et al, 1984, "Induction of Proliferation... Granulocyte Colony-Stimulating Factors", *Blood*, 63(4):904-911.

Rennick et al, 1985, "A Cloned MCGF cDNA...", *J. Immunol.*, 134(2):910-914.

Hapel et al, 1985, "Biologic Properties of Molecularly Cloned and Expressed Murine Interleukin-3", *Blood*, 65(6):1453-1459.

Miyatake et al, 1985, "Structure of the Chromosomal Gene for Murine Interleukin 3", *Proc. Natl. Acad. Sci. USA*, 82:316-320.

Dexter, 1984, "The Message is the Medium", *Nature*, 309:746-747.

Clark-Lewis, 1986, "Automated Chemical Synthesis of ... Interleukin 3", *Science*, 231:134-139 [Chemical Synthesis of Murine IL-3].

Metcalf et al, 1986, "Effects of... Murine... IL-3...", *Blood*, 68(1):46-57.

Birchenall-Sparks et al, Jul. 25, 1986, "Regulation of... by Interleukin-3", *Science*, 233:455-458.

Palacios & Garland, 1984, "... Interleukin 3...", *Proc. Natl. Acad. Sci. USA*, 81:1208-1211.

Scott et al, 1981, "Molecular Cloning...", *Proc. Natl. Acad. Sci. USA*, 78(7):4213-4217.

Quesenberry et al, 1985, "The Effect of Interleukin 3...", *Blood*, 65(1):214-217.

Metcalf et al, 1985, "Synthesis by Mouse...", *Leukemia Research*, 9(1):35-50.

Chen et al, Jul. 15, 1986, "Interleukin 3...", *J. Immunol.*, 137(2):563-570.

Jubinsky et al, 1985, "Purification of Hematopoietin 1...", *Proc. Natl. Acad. Sci.*, USA, 82:2764-2768.

FIGURE 1

```
           10         20         30              49
CTCGAGCTAC GTCAACGAAA AATAAAATCC AAAC ATG AGC TGC CTG CCC GTC CTG CTC
                                     MET Ser Cys Leu Pro Val Leu Leu 64                      79                94                 109
CTG CTC CAA CTC CTG GTC AGC CCC GGA CTC CAA GCT CCC ATG ACC CAG ACA ACG
Leu Leu Gln Leu Leu Val Ser Pro Gly Leu Gln Ala Pro MET The Gln Thr Thr

124                  ┌──139──┐                154
TCC TTG AAG ACA AGC TGG GTT          │AAC TGT TCT│ AAC ATG ATC GAT GAA ATT ATA ACA
Ser Leu Lys Thr Ser Trp Val          │Asn Cys Ser│ Asn Met Ile Asp Glu Ile Ile Thr 169                184                    199                214
CAC TTA AAG CAG CCA CCT TTG CCC TTG CTG GAC TTC AAC AAC CTC AAT GGG GAA
His Leu Lys Gln Pro Pro Leu Pro Leu Leu Asp Phe Asn Asn Leu Asn Gly Glu 229                244                 259                274
GAC CAA GAC ATT CTG ATG GAA AAT AAC CTT CGA AGG CCA AAC CTG GAG GCA TTC
Asp Gln Asp Ile Leu MET Glu Asn Asn Leu Arg Arg Pro Asn Leu Glu Ala Phe

289              ┌──304──┐           319
AAC AAG GCT GTC AAG AGT TTA CAG │AAT GCA TCA│ GCA ATC GAG AGC ATT CTT AAG
Asn Lys Ala Val Lys Ser Leu Gln │Asn Ala Ser│ Ala Ile Glu Ser Ile Leu Lys 334                  349                 364                379
AAT CTC CCC CCA TGC CTG CCC ATG GCC ACA GCC GCA CCC ACG CGA CAT CCA ATC
Asn Leu Pro Pro Cys Leu Pro MET Ala Thr Ala Ala Pro Thr Arg His Pro Ile 394                409                  424
CGT ATC AAG GAC GGT GAC TGG AAT GAA TTC CGG AGG AAA CTG AAG TTC TAT CTG
Arg Ile Lys Asp Gly Asp Trp Asn Glu Phe Arg Arg Lys Leu Lys Phe Tyr Leu 439                454                469                 484
AAA ACC CTT GAG AAT GAG CAA GCT CAA CAG ATG ACT TTG AGC CTT GAG ATC TCT
Lys Thr Leu Glu Asn Glu Gln Ala Gln Gln MET Thr Leu Ser Leu Glu Ile Ser 500        510        520        530        540        550        560
         TGAGTCCAAC GTCCAGCTCT CTCTCTGGGC CGTCTCACCG CAGAGCCTCA GGACATCAAA AACAGCAGAA
             570        580        590       6006       610        620        630
         CTTCTGAAAC CTCTGGGTCG TCTCTCACAC AGTCCAGGAC CAGAAGCATT TCACCTTTTC CTGCGGCATC
             640        650        660        670        680        690        700
         AGATGAATTG TTAATTATCT AATTTCTGAA ATGTGCAGCT CCCATTTGGC CTTGTGTGGT TGTGTTCTCA
             710        720        730        740        750        760        770
         TTTTTATCCC ATTGAGACTA TTTATGTATG TCTGTATTTA TTTATTTATT TATTTATTGC CTTCTGGAGC
             780        790        800        810        820        830        840
         GTGAAGTGTA TTTATTTCAG CAGAGGAGCC ATGTCATGCT GCTTCTGCAA AAAACTCAAG AGTGGGGTGG
             850        860
         GGAGCATGTT CATTTGTACC TCGAG
```

FIGURE 2

```
      A         9           T      24                         39                    A
   GATCCAAAC ATG AGC CGC CTG CCC GTC CTG CTC CTG CTC CAA CTC CTG GTC CGC
             MET Ser Arg Leu Pro Val Leu Leu Leu Leu Gln Leu Leu Val Arg
                 Cys                                 10                        Ser 69                          84                        99
   CCC GGA CTC CAA GCT CCC ATG ACC CAG ACA ACG TCC TTG AAG ACA AGC TGG GTT
   Pro Gly Leu Gln Ala Pro MET Thr Gln Thr Thr Ser Leu Lys Thr Ser Trp Val
                    20                                              30

┌──T──┐              129                 144                       159
       │AAC TGC TCT│ AAC ATG ATC GAT GAA ATT ATA ACA CAC TTA AAG CAG CCA CCT TTG
       │Asn Cys Ser│ Asn MET Ile Asp Glu Ile Ile Thr His Leu Lys Gln Pro Pro Leu
       └───────────┘                   40                                      50

C      ↓174                   189                      204              ↓
   CCT TTG CTG GAC TTC AAC AAC CTC AAT GGG GAA GAC CAA GAC ATT CTG ATG GAA
   Pro Leu Leu Asp Phe Asn Asn Leu Asn Gly Glu Asp Gln Asp Ile Leu MET Glu
                                         60

219                    234                      249     A        264
   AAT AAC CTT CGA AGG CCA AAC CTG GAG GCA TTC AAC AGG GCT GTC AAG AGT TTA
   Asn Asn Leu Arg Arg Pro Asn Leu Glu Ala Phe Asn Arg Ala Val Lys Ser Leu
   70                                               80      Lys

┌─T 279──┐      C    294            G↓    309  CC           C    324
       CAG │AAC GCA TCA│ GCA ATT GAG AGC ATT CTT AAA AAT CTC CTG CCA TGT CTG CCC
       Gln │Asn Ala Ser│ Ala Ile Glu Ser Ile Leu Lys Asn Leu Leu Pro Cys Leu Pro
           └────90────┘                                      100 Pro

A     A       339         ↓        354    G            369
   CTG GCC ACG GCC GCA CCC ACG CGA CAT CCA ATC CAT ATC AAG GAC GGT GAC TGG
   Leu Ala Thr Ala Ala Pro Thr Arg His Pro Ile His Ile Lys Asp Gly Asp Trp
   MET              110                       Arg                120

384                          399  A              414                A   A
   AAT GAA TTC CGG AGG AAA CTG ACG TTC TAT CTG AAA ACC CTT GAG AAT GCG CAG
   Asn Glu Phe Arg Arg Lys Leu Thr Phe Tyr Leu Lys Thr Leu Glu Asn Ala Gln
                         130 Lys                                        Glu

T    450      T   A      C   G    474        T C      494
   GCT CAA CAG ACG ACT TTG AGC CTC GCG ATC TTT T-AGTCCAAC GTCCAGCTCG TTCTCTGGGC
   Ala Gln Gln Thr Thr Leu Ser Leu Ala Ile Phe
                   MET     147         Glu     Ser
                                               152

G     G   A   A       524                     544               G     564
   CTTCTCACCA CAGCGCCTCG GGACATCAAA AACAGCAGAA CTTCTGAAAC CTCTGGGTCA TCTCTCACAC

G              584              604                624
   ATTCCAGGAC CAGAAGCATT TCACCTTTTC CTGCGGCATC AGATGAATTG TTAATTATCT AATTTCTGAA

644                   T         674
   ATGTGCAGCT CCCATTTGGC CTTGTGCGGT TGTGTTCTCA
```

RECOMBINANT DNA ENCODING NOVEL FAMILY OF PRIMATE HEMATOPOIETIC GROWTH FACTORS

CROSS REFERENCE TO RELATED APPLICATIONS

This application is a continuation-in-part of co-owned, commonly assigned U.S. Ser. No. 885,060 filed July 14, 1986, (abandoned) and U.S. Ser. No. 893,764 filed Aug. 6, 1986 (abandoned).

The present invention relates to a novel family of primate IL-3-like hematopoietic growth factors, and a process for producing them by recombinant genetic engineering techniques.

BACKGROUND

Hematopoietins, i.e., hematopoietic growth factors, are proteins that promote the survival, growth and differentiation of hematopoietic cells. Colony stimulating factors (CSFs) are a subset of these hematopoietic growth factors that are characterized by the ability to support the growth, in vitro, of colonies of hematopoietic cells arising from progenitor cells of bone marrow, fetal liver and other hematopoietic organs.

The biochemical and biological identification and characterization of certain hematopoietins has been hampered by the small quantities of the naturally occurring factors available from natural sources, e.g., blood and urine. With recombinant genetic engineering techniques, however, some of these hematopoietins have been molecular cloned, heterologously expressed and purified to homogeneity. [See D. Metcalf, "The Molecular Biology and Functions of the Granulocyte-Macrophage Colony Stimulating Factors," Blood, 67(2):257-267 (1986).] Among these hematopoietins are human and murine GM-CSF, human G-CSF, human CSF-1 and murine IL3. Both human GM-CSF [See, R. Donahue et al., Nature, 321:872-875 (1986)] and murine IL3 [See J. Kindler et al, Proc. Natl. Acad. Sci. U.S.A., 83:1001-1005 (1986)] have a demonstrated effect on hematopoiesis in vivo. The murine protein IL-3 has heretofore been found to have no duplicate in the human system. [See, D. R. Cohen et al, Nucl. Acids Res., 14:3641 (1986).]

BRIEF SUMMARY OF THE INVENTION

As one aspect of the invention, a family of primate IL-3-like growth factors are provided which are characterized by amino acid sequences substantially homologous to the sequence shown in FIGS. I and II below. The amino acid sequences of the growth factors of the present invention are encoded by the DNA sequences of FIGS. I and II. Additionally, members of this family of growth factors are coded for by DNA sequences which hybridize under stringent hybridization conditions to the DNA sequences of FIGS. I and II.

DNA sequences which hybridize to the sequences of FIGS. I or II under relaxed hybridization conditions and which code on expression for growth factors having IL-3-like biological properties also encode members of this family of novel growth factors. For example, a DNA sequence which shares regions of significant homology, e.g., sites of glycosylation or disulfide linkages, with the sequences of FIGS. I and/or II and encodes a primate protein having one or more IL-3-like biological properties clearly encodes a member of this novel family of growth factors, even if such a DNA sequence would not stringently hybridize to the sequence of FIGS. I or II.

Similarly, DNA sequences which code for polypeptides coded for by the sequence of FIGS. I or II or sequences which hybridize thereto, but which differ in codon sequence due to the degeneracies of the genetic code or differ in nucleotide sequence due to cross-species variation or induced modifications also encode the novel growth factors of this family described herein.

In addition to the DNA sequence homology to the sequences of FIGS. I and II, the members of this novel family of growth factors are also characterized by having at least one biological property of an IL-3-like growth factor. Preferably more than one IL-3-like biological property is demonstrated by any one member of the family of growth factors of the present invention. "IL-3-like biological property" is defined herein to include one or more of the following biological characteristics and in vivo and in vitro activities. One such property is the support of the growth and differentiation of progenitor cells committed to erythroid, lymphoid, and myeloid lineages. For example, in a standard human bone marrow. assay, an IL-3-like biological property is the stimulation of granulocytic type of linies aid erythroid bursts Another such property is the interaction with early multipotential stem cells. An IL-3-like biological property is the sustaining of the growth of pluripotent precurser cells. Another property is the ability to stimulate chronic myelogenous leukemia (CML) cell proliferation. An IL-3-like biological property also is the stimulation of proliferation of mast cells IL-3-like growth factors may also support the growth of various factor-dependent cell iines and/or induce the expression of 20-alpha-steroid dehydrogenase (20-alpha-SPH) and Thy-1 antigen. Further IL-3-like biological properties are the stimulation of colony formation on KG-1 cells and/or the stimulation of increased histamine synthesis in spleen and bone marrow cultures. Yet another IL-3 biological property is an apparent molecular weight of between about 14 to about 35 kd by reducing sodium dodecyl sulfate polyacrylamide gel electrophoresis. Other biological properties of IL-3 have been disclosed in the art.

As a further aspect of the present invention there are provided novel DNA sequences coding on expression for primate IL-3-like polypeptides or growth factors. These DNA sequences include those depicted in FIGS. I and II in a 5' to 3' direction and those sequences described above. Variations in the DNA sequences of FIGS. I and II which are caused by point mutations or by induced modifications to enhance the activity or production of the polypeptides are also encompassed in the invention. Similarly, synthetic polypeptides which wholly or partially duplicate continuous sequences of the amino acid residues of FIGS. I and II are also part of this invention. These sequences, by virtue of sharing primary, secondary or tertiary structural and conformational characteristics with naturally-occurring primate IL-3-like polypeptides of the invention may possess biological activity and/or immunological properties in common with the naturally-occurring product. Thus, they may be employed as biologically active or immunological substitutes for naturally-occurring primate IL-3-like polypeptides in therapeutic and immunological processes.

As another aspect of the present invention, there is provided a novel method for producing the novel family of primate IL-3-like growth factors. The method of the present invention involves culturing a suitable cell or cell line, which has been transformed with a vector containing a DNA sequence coding on expression for a novel primate IL-3-like polypeptide. Suitable cells or cell lines may be mammalian cells, such as Chinese hamster ovary cells (CHO). Another suitable mammalian cell line, which is described in the accompanying examples, is the monkey COS-1 cell line. A similarly useful mammalian cell line is the CV-1 cell line. Also suitable for use in the present invention are bacterial cells. For example, the various strains of E. coli are well-known as host cells in the field of biotechnology. Various strains of B. subtilis may also be employed in this method. Many strains of yeast cells known to those skilled in the art are also available as host cells for expression of the polypeptides of the present invention. Additionally, where desired, insect cells may be utilized as host cells in the method of the present invention.

Another aspect of the present invention provides vectors for use in the method of expression of these novel primate polypeptides. These vectors contain the novel DNA sequences described above which code for the novel polypeptides of the invention. Alternatively, vectors incorporating modified sequences as described above are also embodiments of the present invention and useful in the production of these IL-3-like polypeptides. The vector employed in the method also contains selected regulatory sequences in operative association with the DNA coding sequences of the invention and capable of directing the replication and expression thereof in selected host cells.

The members of the novel family of primate IL-3-like growth factors may be used in the treatment of diseases characterized by a decreased level of either myeloid, erythroid, lymphoid or megakaryocyte cells of the hematopoietic system or combinations thereof. In addition they may be used to activate mature myeloid and/or lymphoid cells. Among conditions susceptible to treatment with the polypeptides of the present invention is leukopenia, a reduction in the number of circulating leucocytes (white cells) in the peripheral blood. Leukopenia may be induced by exposure to certain viruses or to radiation. It is often a side effect of various forms of cancer therapy, e.g., exposure to chemotherapeutic drugs. Therapeutic treatment of leukopenia with these IL-3-like polypeptide compositions may avoid undesirable side effects caused by treatment with presently available drugs.

Various immunodeficiencies e.g., in T and/or B lymphocytes, may also be corrected by treatment with the polypeptides of the present invention. Immunodeficiencies may be the result of viral infections e.g. HTLVI, HTLVII, HTLVIII, severe exposure to radiation, cancer therapy or the result of other medical treatment The polypeptides of the present invention may also be employed, alone or in combination with other hematopoietins, in the treatment of other blood cell deficiencies, including thrombocytopenia (platelet deficiency), or anemia (red cell deficiency) Other uses for these novel polypeptides are in the treatment of patients recovering from bone marrow transplants, and in the development of monoclonal and polyclonal antibodies generated by standard methods for diagnostic or therapeutic use.

Therefore, as yet another aspect of the invention are therapeutic compositions for treating the conditions referred to above. Such compositions comprise a therapeutically effective amount of one or more of the members of the family of primate IL-3-like polypeptides of the present invention in admixture with a pharmaceutically acceptable carrier. This composition can be systematically administered either parenterally, intravenenously or subcutaneously. When systematically administered, the therapeutic composition for use in this invention is, of course, in the form of a pyrogen-free, parenterally acceptable aqueous solution. The preparation of such a parenterally acceptable protein solution, having due regard to pH, isotonicity, stability and the like, is within the skill of the art.

The dosage regimen will be determined by the attending physician considering various factors which modify the action of drugs, e.g. the condition, body weight, sex, and diet of the patient, the severity of any infection, time of administration and other clinical factors. Generally, the daily regimen should be in the range of 200–1000 micrograms of polypeptide or 50 to 5000 units (i.e., a unit being the concentration of polypeptide which leads to half maximal stimulation in a standard human bone marrow assay) of polypeptide per kilogram of body weight. This therapeutic composition may also be administered in conjunction with other human factors. A non-exclusive list of other appropriate hematopoietins, CSFs and interleukins for interaction with the polypeptides of the present invention includes GM-CSF, CSF-1, G-CSF, Meg-CSF, erythropoietin (EPO), IL-1, IL-4, IL-2, B-cell growth factor, B-cell differentiation factor and eosinophil differentiation factor. The dosage recited above would be adjusted to compensate for such additional components in the therapeutic composition. Progress of the treated patient can be monitored by periodic assessment of the hematological profile, e.g. white cell count and the like.

DETAILED DESCRIPTION OF THE INVENTION

The present invention provides a family of primate IL-3-like growth factors characterized by amino acid sequences substantially homologous to the amino acid sequences illustrated in FIGS. I and II below. These sequences may be encoded by the DNA sequences depicted in the Figures or sequences capable of hybridizing thereto and coding for polypeptides with IL-3-like biological properties or variously modified sequences as described above. These polypeptides are also characterized by IL-3-like biological properties.

The specific sequences illustrated in FIGS. I and II are two exemplary members of the growth factor family of the present invention. The 865bp DNA sequence of FIG. I was isolated from a cDNA expression library of the gibbon ape leukemia virus infected gibbon T-cell line UCD-144-MLA [T. G. Kuwakami et al, Nature, 235:170 (1972)]. This sequence contains a single long open reading frame of 456 nucleotides which encodes an approximately 152 amino acid protein, called CSF-80, and includes a conventional leader secretory sequence indicated by the highly hydrophobic sequence (leu leu leu leu gln leu leu) The mature protein begins at amino acid number 20, alanine, in FIG. I. The coding region contains three cysteines, two in the mature protein, thereby suggesting one disulfide bond. There are two potential asparagine-linked glycosylation sites illustrated by the characteristic sequences, Asn-X-Ser or Asn-X-Thr. Both the size and glycosylation pattern revealed by the coding sequence are typical of lymphokine-like proteins. The remaining non-coding portions of the 865bp region may have a regulatory role in transcription in the natural host. The 3' end of the sequence also contains an AT-rich segment including several repeats of the sequence ATTTA, which is believed to be related to the RNA message stability [See, Shaw and Kamen, Cell, 46(5):659–677(1986).

The 674bp DNA sequence of FIG. II was obtained from a human genomic library [J. J. Toole et al, Nature, 312:342–346 (1984)] by employing the sequence of FIG. I as a probe. The DNA sequence of FIG. II was constructed by splicing together the exons of the human genomic sequence, which were identified by comparison with the DNA sequence of the gibbon IL-3-like polypeptide of FIG. I This human sequence also codes for a putative polypeptide of approximately 152 amino acids, which is a member of this family of primate proteins. This putative human polypeptide includes a conventional leader secretory sequence indicated by the highly hydrophobic sequence (leu leu leu leu gln leu leu). The mature polypeptide begins at amino acid number 20, alanine, in FIG. II. The coding region contains two cysteines in the mature protein, suggesting one disulfide bond. There are two potential asparagine-linked glycosylation sites illustrated by the characteristic sequence, Asn-X-Ser. The remaining non-coding portions of the 674bp sequence may have a regulatory role in transcription in the natural host.

The nucleotide sequences of the exons of the human genomic gene [FIG. II] were more than 99.5% homologous with the DNA sequence of the gibbon gene [FIG. I]. Changes. in the nucleotide sequences in 11 codons result in amino acid differences in the gibbon and human proteins. The nucleotides appearing above the sequence of FIG. II indicate the sites where the gibbon sequence differs from the related human sequence Similarly, the amino acids appearing below the human amino acid sequence indicate where the gibbon sequence differs. The arrows indicate the predicted sites of exon and intron junctions in the human genomic sequence.

A computer search by National Biomedical Services of Washington, D.C. revealed that the gibbon and human IL-3-like sequences have approximately 29% homology at the amino acid level and 45% homology at the nucleotide level to the murine IL-3 DNA sequence, as published by M. C. Fung et al , Nature, 307:233–237 (1984). These exemplary members of the primate family of IL-3-like polypeptides are thus proteins related to murine IL-3 and may demonstrate the multi-potential CSF activities attributed to murine IL-3. [See A. J. Hapel et al., Blood, 65:1453–1459 (1985) and J. Kindler et al, supra.] These activities include the promotion, in vivo, of the survival, growth and differentiation of myeloid, erythroid and lymphoid lineages, e.g., granulocyte-macrophage, eosinophil, megakarocyte, natural killer-like cells, T lymphocytes, B lymphocytes, basophils, erythroid cells and mast cells.

A comparison of the exon structure of this human IL-3-like gene of FIG. II with that of murine IL-3 illustrates the relatedness of the genes. The coding regions of both proteins comprise five exons of very similar size. The two human introns whose sequences have been determined are also very similar in size to the corresponding murine introns. These results further illustrate that the exemplary gibbon and human genes of FIGS. I and II respectively are related to the gene for murine IL-3.

The novel 865bp cDNA sequence illustrated in FIG. I below, included in plasmid in E. coli HB101, has been deposited in the American Type Culture Collection, 12301 Parklawn Dr., Rockville, MD and given accession number ATCC 67154. The novel genomic sequence, for which the putative cDNA sequence is illustrated in FIG. II below, included in bacteriophage lambda, has been similarly deposited and given accession number ATCC 40246.

The exemplary gibbon IL-3-like polypeptide, CSF-80, has been further characterized by an apparent molecular weight of between about 14kd-35kd when analyzed by polyacrylamide gel electrophoresis under reducing conditions. The protein, at 10 to 100 picomolar concentrations, causes the formation of small granulocytic-type colonies in in vitro human bone marrow assays, characteristic of a CSF protein. Additionally, in the presence of erythropoietin in these human bone marrow assays, CSF-80 supports the growth of erythroid progenitor cells. Thus like murine IL-3, CSF-80 is a multi-CSF. CSF-80 also causes the proliferation of leukemic blast cells from patients with CML. This polypeptide may also be capable of stimulating accessory and mature cells, e.g. monocytes, to produce other hematopoietic-like factors, which in turn stimulate the formation of colonies of other hematopoietic cells, as well as other hematopoietic-type activities.

The family of IL-3-like growth factors provided herein also includes factors encoded by the sequences of FIGS. I and II into which nucleotide modifications have been deliberately engineered. Such modifications in the DNA sequences can be made by one skilled in the art using various techniques. Specific modifications of interest in these IL-3-like related sequences include the replacement of one or both of the two cysteine residues in each coding sequence with other amino acids Preferably both cysteines are replaced with another amino acid, e.g. serine, to eliminate the disulfide bridge. Mutagenic techniques for such replacement are well known to one skilled in the art. [See, e.g., U.S. Pat. No. 4,518,584.]

Other specific mutations of the sequences of the IL-3-like factors described herein involve modifications of one or both of the glycosylation sites. The absence of glycosylation or only partial glycosylation results from amino acid substitution at one or both of the asparagine-linked glycosylation recognition sites present in the sequences of the IL-3-like factors shown in FIGS. I and II. The asparagine-linked glycosylation recognition sites comprise tripeptide sequences which are specifically recognized by appropriate cellular glcosylation enzymes. These tripeptide sequences are either asparagnne-X-threonine or asparagine-X-serine, where X is usually any amino acid. A variety of amino acid substitutions at one or more of the three amino acid positions of a glycosylation recognition site, especially the first and/or third such positions, results in non-glycosylation at the modified tripeptide sequence. By way of example, $Asn_{34}$ of the sequence of FIG. I can be replaced with glutamine in one such modified IL-3-like factor. The resulting factor ($Gln_{34}$) should contain only one asparagine-linked carbohydrate moiety (at $Asn_{89}$), rather than two such moieties. Those skilled in the art will appreciate that analogous glycoproteins having the same $Asn_{89}$ monoglycosylation may be prepared by substituting another amino acid at position 34, and/or by substituting another amino acid at the other positions within the glycosylation recognitions site, e.g., inserting valine at $Ser_{36}$. Similarly, the Asn at position 89 and/or Ser at position 91 may be altered by a mutagenic technique to other amino acids to deglycosylate the factor at that site. Alternatively, both sites may be altered as above. Such modifications to the glycosylation sites may also be made to create modifications of the sequence of FIG. II. [See, e.g. A. Miyajima et al., *EMBO J.*, 5(6):1993-1197 (1986).]

The following examples illustratively describe members of the novel family of primate IL-3-like polypeptides and the methods of the present invention.

EXAMPLE I

Isolation of CSF-80 DNA Sequence

A gibbon T-cell line infected with gibbon-ape leukemia virus, UCD-144-MLA, and available from the National Institute of Health Laboratories was induced with phytohemagglutinin and phorbol. myristate acetate (PHA/PMA). Total RNA was prepared from these cells by the procedures of J. M. Chirgwin et al., *Biochem*, 18:5294 (1979). Poly A+ mRNA was selected and fractionated on a 10% to 30% sucrose gradient. To identify the mRNA encoding this novel hematopoietic factor, sixteen aliquots of sucrose gradient-fractionated mRNA from the UCD-144-MLA cell line were microinjected into *Xenoous laevis* oocytes and the resulting conditioned medium tested for the ability to stimulate the proliferation of leukemic blast cells in the presence of antibody to human GM-CSF as illustrated in the CML assay of Example V. mRNA from the sucrose gradient fractions identified as containing the message encoding IL-3-like growth factor activity was converted to double stranded cDNA by the procedure of U. Gubler and B. J. Hoffman, *Gene*, 25 263 (1983).

A COS cell expression vector, pXM, containing the SV40 enhancer, major adenovirus late promoter, DHFR coding sequence, SV40 late message poly A addition site and VaI gene was linearized with the endonuclease enzyme XhoI, treated with DNA polymerase I large fragment in the presence of dTTP and ligated to equimolar amounts of cDNA, at a final DNA concentration of 100 ug/ml. The ligation products resulting from the XhoI digestion of pXM and the insertion of the XhoI adapted cDNA sequence were transformed into *E. coli* strain HB101 and plated on L+ Amp plates to generate a library of approximately 30×10³ colonies.

The cDNA library in pXM was replica plated onto nitrocellulose filters. Colonies from each filter were scraped into L. broth, and plasmid DNA was isolated. Each DNA sample was prepared from a pool of 200-300 bacterial colonies. The DNA was purified by the method of J. A. Meyers et al., *J. Bacteriol*, 127:1529 (1976). Monkey COS cells (ATCC CRL 1650) were transfected with approximately 5 ug plasmid DNA per 10⁶ COS cells by DEAE mediated DNA transfection and treated with chlorquine according to the procedures described in G. G. Wong et al., *Science*: 228:810-815 (1985) and R. J. Kaufman et al. Mol. Cell Biol., 2:1304 (1982).

72 hours following transfection, medium is harvested and assayed in the human CML assay, as described in Example V below. One pool produced conditioned medium with colony stimulating activity and CML proliferation activity completely resistant to neutralizing antiserum to GMCSF, and was selected for further analysis Plasmid DNA from individual colonies picked from the original active pool was prepared and transfected to produce conditioned medium. This conditioned medium was assayed for CSF and CML proliferation activity. A single clone responsible for such activity was isolated. The cDNA insert of this clone was subcloned into M13 and was sequenced by the Sanger dideoxy chain termination method. [See FIG. I]

EXAMPLE II

Analysis of a Human IL-3-like Gene

Using the sequence of FIG. I as a probe, 1×10⁶ clones from a human genomic library (Sau 3AI partial digest of human DNA cloned into the Bam HI site of the lambda vector JI) [J. J. Toole et al, supra] were screened. Three plaques were identified which contained sequences which hybridized strongly with the cDNA probe. The DNAs from two of these phages were digested to completion with the endonuclease enzyme Sau 3AI and subcloned into the Bam HI site of the bacteriophage lambda M13 cloning vector mp9. Subclones containing exon sequences were identified by hybridization with the CSF-80 cDNA. One subclone, lambda CSF-16, containing the human genomic DNA sequence as an approximately 10kb Bgl II insert, was deposited with the ATCC. The complete sequences of all of the exons of the human gene were determined using dideoxy chain termination DNA sequencing with a battery of oligonucleotide primers whose sequences were based upon the sequence of the gibbon gene described in Example I. Because the nucleotide sequences of the exons of the human gene were more than 99.5% homologous with the sequence of the gibbon cDNA, the nucleotide sequence of the corresponding putative human cDNA was reconstructed. Changes in the nucleotide sequences in 11 codons result in amino acid differences in the polypeptides from the two species. [See FIG. II].

EXAMPLE III

Expression of An Exemplary Gibbon Member of the Primate IL-3-like Growth Factor Family A plasmid, pCSF-MLA, is simply constructed by inserting the sequence of FIG. I into XhoI-digested pXM as described above. pCSF-MLA is then transformed by conventional techniques into a selected host cell for expression of a polypeptide, CSF-80. Exemplary host cells are mammalian cells and cell lines, particularly primate cell lines, rodent cell lines and the like. To obtain expression of CSF-80 for use in the assays of Example V, pCSF-MLA was transfected onto COS cells and harvested as described above.

One skilled in the art can also construct other mammalian expression vectors comparable to pCSF-MLA by, e.g., cutting the DNA sequence of FIG. I from the plasmid with XhoI and employing well-known recombinant genetic engineering techniques and other known vectors, such as pCD [Okayama et al., *Mol Cell Biol.* 2:161-170 (1982)]and pJL3, pJL4 [Gough et al., *EMBO J.*, 4:645-653 (1985)]. The transformation of these vectors into appropriate host cells can result in expression of CSF-80.

Similarly, one skilled in the art could manipulate the sequences of FIG. I by eliminating or replacing the mammalian regulatory sequences flanking the coding sequence with bacterial sequences to create bacterial vectors for intracellular or extracellular expression by bacterial cells. For example, the coding sequence of FIG. I could be cut from pCSF-MLA with XhoI and further manipulated (e.g., ligated to other known linkers or modified by deleting non-coding sequences there-from or altering nucleotides therein by other known techniques). The modified IL-3-like coding sequence could then be inserted into a known bacterial vector using procedures such as described in T. Taniguchi et al., *Proc Natl Acad. Sci. USA,* 77:5230-5233 (1980). This exemplary bacterial vector could then be transformed into bacterial host cells and CSF-80 expressed thereby. For a strategy for producing extracellular expression of CSF-80 in bacterial cells, see, e.g. European patent application EP 177,343.

Similar manipulations can be performed for the construction of an insect vector [See, e.g., procedures described in published European patent application 155,476] for expression in insect cells. A yeast vector could also be constructed employing yeast regulatory sequences for intracellular or extracellular expression of the proteins of the present inventions by yeast cells. [See, e.g., procedures described in published PCT application WO 86 00639 and European patent application EP 123,289.]

EXAMPLE IV

Expression of An Exemplary Human Member of the Primate IL-3-Like Growth Factor Family The putative cDNA sequence for a human IL-3-like polypeptide as indicated in FIG. II for use in the construction of an expression vector may be obtained in three ways. Firstly, the sequence of FIG. II may be chemically synthesized according to procedures well known to those skilled in the art.

Alternatively, the human genomic sequence may be excised as a Bgl II fragment from the deposited bacteriophage, lambda CSF-16, cloned in a plasmid expression vector, eg. pXM, by standard molecular biology techniques and amplified in bacteria The expression vector containing the gene is then transfected into a mammalian cell, e.g., monkey COS cells, where the human gene is transcribed and the RNA correctly spliced. Media from the transfected cells is assayed for IL-3-like biological properties as described above as an indication that the gene is complete mRNA is obtained from these cells and cDNA synthesized from the mRNA by standard procedures. The respective human cDNA for a novel IL-3-like growth factor can be isolated.

A third method for obtaining the cDNA sequence of this human IL-3-like growth factor involves cloning the cDNA from a tissue source. The gibbon cDNA sequence of FIG. I was employed as a probe according to T. Maniatis et al., Molecular Cloning—A Laboratory Manual, Cold Spring Harbor Laboratory, (1983) and identified peripheral blood lymphocytes as a human source for isolating mRNA encoding this human IL-3-like polypeptide Poly A+ RNA is prepared from the peripheral blood lymphocyte source, converted to cDNA and cloned as either a phage or plasmid cDNA library A human cDNA clone can be identified by hybridization with the gibbon coding sequence of FIG. I as a DNA probe and a determination of IL-3-like biological properties.

Additional tissue sources which may also be screened for human IL-3-like cDNA include spleen, liver, thymus, tonsils, kidney and other fresh tissues available from biopsies and cadavers. Of special interest are cases where the tumor may be responsible for elevated hematopoietic cell counts, e.g., leukemia. Additional sources are the cell lines deposited for public use in depositories, e.g. ATCC, or available through government agencies and certain private sources. Exemplary cell lines include transformed T and B cell lines, and cell lines which are not of hematopoietic origin, but generate hematopoietins.

In order to express this human IL-3-like polypeptide, the cDNA encoding it is transferred into an appropriate expression vector and introduced into selected host cells by conventional genetic engineering techniques as described above for the gibbon IL-3-like polypeptide in Example III. The presently preferred expression system for a biologically active recombinant human IL-3-like polypeptide is stably transformed CHO cells. However, an active polypeptide may be produced intracellularly or extracellularly from bacteria, yeast or insect cells as described in Example III.

Another alternative method for expressing this human IL-3-like polypeptide is to employ the Bgl II fragment from lambda CSF-16 containing the complete human genomic gene to construct mammalian cell lines expressing the polypeptide, e.g. as described by PCT WO85/20610 for human erythropoietin In addition, this human genomic gene can be engineered with the appropriate promoter and processing signals for expression in some other heterologous system, e.g. insect promoters for constructing insect cell culture lines. Similarly, this genomic gene may be expressed in yeast or other eukaryotic systems.

EXAMPLE V

In Vitro Activities of a Gibbon IL-3-like Polypeptide

The following assays were performed using a gibbon polypeptide as a representative member of the novel family of primate IL-3-like polypeptides of the present invention. However, other members of the family, including the human IL-3-like polypeptides will exhibit IL-3-like biological properties in these same assays or in other assays depending on the number of IL-3-like biological properties displayed by the individual polypeptide.

A. CML Assay

The CML assay was performed essentially according to procedures described in *Blood,* 63(4):904–111 (1984). A stock of cells were obtained from a frozen bag of peripheral blood from a CML patient in stable phase. This bag was thawed and refrozen into 500 aliquots of $15 \times 10^6$ cells/vial. These cells, "CML 8-3", were used to test for the IL-3-like activity of the gibbon polypeptide. One vial is thawed quickly at 37° C. the day before the assay is set up. The contents of the vial are then transferred to a 15 ml tube and washed 2 times with 5% Hi Human AB Serum in RPMI (GIBCO,RPMI 1640) [HAB/RPMI]. The cells are incubated overnight in 5% HiHAB RPMI at 5% $CO_2$ and 37° C. The following day the cells are removed from culture, ficolled, washed, recounted and set aside.

100 ul of 10% HIFCS2/RPMI medium containing the material to be assayed is plated in each well of a microtiter plate. The cells prepared above are spun down and resuspended at a concentration of 1.3 to $2 \times 10^5$ cells/ul in 10% HIFCS/RPMI. 100 uls of cells are plated in each well and incubated in the presence or absence of anti-human GMCSF antibodies at 37° C. in 5% $CO_2$ for 48 or 72 hours. Thereafter 0.5 uCi $^3$H-thymidine is added per well and the wells are incubated for 6 hours at 37° C. Cells are harvested using a filtration manifold device onto GFC Type C filter paper (Schleicher-Schuller), washed with phosphate buffered saline and dried. Filters are then immersed in scintillation fluid and counted for $^3H$ uptake. Based on the thymidine uptake measurement, the gibbon IL-3-like growth factor of FIG. I is active in this assay in stimulating the proliferation leukemic blast cells pCSF-MLA conditioned medium containing the polypeptide was found to be active up to at least 62,500 fold dilution in the CML assay.

B. Bone Marrow Assays

Human bone marrow assays, employing non-adherent bone marrow cells, were performed as described in G. G. Wong, et al., supra. pCSF-MLA conditioned medium was found to be active in this assay, producing small colonies of apparently granulocytic-type lineage When this assay is performed in the presence of erythropoietin, the ability of conditioned medium to support the growth of erythroid progenitor cells is demonstrated by the production of red blood cell colonies However, pCSF-MLA was not active in the standard murine bone marrow assay.

C. KG-1 Cell Assay

The KG-1 assay was performed as described in G. G. Wong et al, supra. The gibbon IL-3-like polypeptide member of the novel primate family of IL-3-like growth factors produced according to the present invention was active in this assay.

EXAMPLE VI

Molecular Weight Analysis of A Gibbon IL-3-Like Polypeptide

Following the procedure of R. J. Kaufman and P. A. Sharp., J. Mol. Biol. 159:601–629 (1982), $^{35}S$ methionine is metabolically incorporated into the gibbon polypeptide made by COS cells transfected with pCSF-MLA DNA. SDS polyacrylamide gel electrophoresis (reducing conditions) [U. K. Laemmli, Nature 227:680–685 (1970)] of labeled proteins secreted by the transfected COS-1 cells revealed a distribution of polypeptides with apparent molecular masses ranging between 14kd and 35kd. This distribution was absent in the mock transfected control sample.

EXAMPLE VII

Construction of CHO cell lines expressing which levels of a Primate IL-3-like Growth Factor One method for producing high levels of a member of the novel primate family of IL-3-like polypeptides of the invention from mammalian cells involves the construction of cells containing multiple copies of the heterologous gene. The heterologous gene can be linked to an amplifiable marker, e.g., the dihydrofolate reductase (DHFR) gene for which cells containing increased gene copies can be selected for propagation in increasing concentrations of methotrexate (MTX) according to the procedures of Kaufman & Sharp, J. Mol. Biol., supra. This approach can be employed with a number of different cell types.

For example, pCSF-MLA contains a gibbon IL-3-like gene in operative association with other plasmid sequences enabling expression thereof. pCSF-MLA and the DHFR expression plasmid pAdA26SV (A)3 (Kaufman & Sharp, Mol. Cell Biol., supra) can be co-introduced into DHFR-deficient CHO cells, DUKX-BII, by calcium phosphate coprecipitation and transfection DHFR expressing transformants are selected for growth in alpha media with dialyzed fetal calf serum, and subsequently selected for amplification by growth in increasing concentrations of MTX (sequential steps in 0.02, 0.2, 1.0 and 5uM MTX) as described in Kaufman, et al., Mol. Cell Biol, 5:1750 (1983). Transformants are cloned, and biologically active IL-3-like polypeptide expression is monitored by CML assays. IL-3-like polypeptide expression should increase with increasing levels of MTX resistance. Similar procedures can be followed to produce other members of this family of IL-3-like polypeptides, including the human IL-3-like polypeptides.

Numerous modifications and variations in practice of this invention are expected to occur to those skilled in the art upon consideration of the foregoing descriptions of preferred embodiments thereof Such modifications and variations are believed to be encompassed in the appended claims.

What is claimed is:

1. A recombinant DNA sequence comprising vector DNA and an isolated DNA that encodes a polypeptide comprising one of the mature peptide sequences as shown in FIG. I or FIG. II and which possesses at least one of the biological properties of primate IL-3, said biological properties being selected from the group consisting of:
   (a) the ability to support the growth and differentiation of primate progenitor cells committed to erythroid, lymphoid and myeloid lineages;
   (b) the ability to stimulate granulocytic colonies and erythroid bursts in a standard human bone marrow assay;
   (c) the ability to sustain the growth of primate pluripotent precurser cells; and,
   (d) the ability, at 10 to 100 picomolar concentrations, to stimulate primate chronic myelogenous leukemia (CML) cells in the CML assay.

2. A recombinant DNA sequence comprising vector DNA and an isolated DNA capable of hybrtidizing under stringent conditions, or which would be capable of hybridizing under said conditions but for the degeneracy of the genetic code, to DNA sequence selected from the group consisting of:
   (a) the DNA sequence of FIG. I;
   (b) the DNA sequence of FIG. II;
   (c) the XhoI insert in pXM (ATCC 671540; and
   (d) the Bam HI or Bgl II genomic insert in bacteriophage lambda M13 cloning vector mp9 (ATCC 40246);

said isolated DNA encoding a polypeptide having at least one biological property of primate IL-3 selected from the group consisting of:
   (i) the ability to support the growth and differentiation of primate progenitor cells committed to erythroid, lymphoid and myeloid lineages;
   (ii) the ability to stimulate granulocytic colonies and erythroid bursts in a standard human bone marrow assay;
   (iii) the ability to sustain the growth of primate pluripotent precursor cells; and,
   (iv) the ability, at 10 to 100 picomolar concentrations, to stimulate primate chronic myelogenous leukemia (CML) cells in the CML assay.

3. A recombinant DNA sequence of claim 1 wherein the isolated DNA comprises a cDNA.

4. A recombinant DNA sequence of claim 2 wherein the isolated DNA comprises a cDNA.

5. A recombinant DNA vector comprising a DNA sequence that encodes a polypeptide comprising a mature peptide sequence as shown in FIG. I or FIG. II an possessing at least one of the biological properties of primate IL-3, said biological properties being selected from the group consisting of:
  (a) the ability to support the growth and differentiation of primate progenitor cells committed to erythroid, lymphoid and myeloid lineages;
  (b) the ability to stimulate granulocytic colonies and erythroid bursts in a standard human bone marrow assay;
  (c) the ability to sustain the growth of primate pluripotent precursor cells; and,
  (d) the ability, at 10 to 100 picomolar concentrations, to stimulate primate chronic myelogenous leukemia (CML) cells in the CML assay
wherein said vector contains a regulatory sequence operatively associated with said DNA sequence which is capable of directing the replication and expression thereof in a host cell.

6. A recombinant DNA vector of claim 5 wherein said DNA sequence is a cDNA.

7. A host cell containing a recombinant DNA sequence of claims 1, 2, 3, or 4, or a recombinant DnA vector of claims 5 or 6 and capable of expressing the encoded polypeptide.

8. A method for producing a polypeptide that has at least one primate IL-3 biological property comprising the steps of:
  (1) culturing a cell of claim 7 wherein the recombinant DNA vector contained therein has been prepared by isolating the DNA sequence encoding primate IL-3 and operably linking it to an expression control sequence, or the progeny thereof, under conditions permitting expression of the recombinant DNA; and,
  (2) harvesting the polypeptide from the culture.

9. A recombinant DNA vector comprising an isolated DNA sequence encoding a polypeptide comprising the mature peptide sequence of Figure II, the DNA sequence being operatively linked to an expression control sequence therefor.

10. A host cell or cell line containing the DNA vector of claim 9.

11. A DNA vector of claim 9 comprising the BglII fragment of ATCC No. 40246, which encodes human IL-3.

12. A method of making a primate IL-3 polypeptide comprising culturing a host cell or cell line of claim 10 wherein the recombinant DNA vector contained therein has been prepared by isolating the DNA sequence encoding primate IL-3 and operably linking it to an expression control sequence under conditions permitting expression of the recombinant DNA; and harvesting the polypeptide from the culture.

* * * * *